(12) United States Patent
Akiyama et al.

(10) Patent No.: US 10,248,003 B2
(45) Date of Patent: Apr. 2, 2019

(54) NON-LINEAR OPTICAL CRYSTAL AND METHOD FOR MANUFACTURING SAME, AND TERAHERTZ-WAVE GENERATOR AND TERAHERTZ-WAVE MEASURING APPARATUS

(71) Applicant: HAMAMATSU PHOTONICS K.K., Hamamatsu-shi, Shizuoka (JP)

(72) Inventors: Kouichiro Akiyama, Hamamatsu (JP); Yoichi Kawada, Hamamatsu (JP); Takashi Yasuda, Hamamatsu (JP); Atsushi Nakanishi, Hamamatsu (JP); Hironori Takahashi, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 0 days.

(21) Appl. No.: 15/505,963

(22) PCT Filed: Aug. 28, 2015

(86) PCT No.: PCT/JP2015/074410
§ 371 (c)(1),
(2) Date: Feb. 23, 2017

(87) PCT Pub. No.: WO2016/035702
PCT Pub. Date: Mar. 10, 2016

(65) Prior Publication Data
US 2017/0248833 A1    Aug. 31, 2017

(30) Foreign Application Priority Data

Sep. 2, 2014    (JP) ................................. 2014-178042

(51) Int. Cl.
*G02F 1/355*    (2006.01)
*G02F 1/361*    (2006.01)
(Continued)

(52) U.S. Cl.
CPC .......... *G02F 1/3612* (2013.01); *C07C 309/30* (2013.01); *C07D 213/38* (2013.01);
(Continued)

(58) Field of Classification Search
CPC .... G02F 1/3612; G02F 1/3551; G02F 1/3613; G01N 21/3581
(Continued)

(56) References Cited

U.S. PATENT DOCUMENTS

2014/0061474 A1*    3/2014    Kitamura .................. G01J 3/42
250/339.02

FOREIGN PATENT DOCUMENTS

JP    2005-284232 A    10/2005
JP    2007-328145 A    12/2007
(Continued)

OTHER PUBLICATIONS

S. Brahadeeswaran, Y. Takahashi, M. Yoshimura, M. Tani, S. Okada, S. Nashima, Y. Mori, M. Hangyo, H. Ito, and T. Sasaki, Growth of Ultrathin and Highly Efficient Organic Nonlinear Optical Crystal 4'-Dimethylamino-N-methyl-4-Stilbazolium p-Chlorobenzenesulfonate for Enhanced Terahertz Efficiency at Higher Freq., Cryst. Growth Des. 2013,13, 415-421.*
(Continued)

*Primary Examiner* — Bijan Ahvazi
(74) *Attorney, Agent, or Firm* — Drinker Biddle & Reath LLP (57) ABSTRACT

Disclosed is a non-linear optical crystal containing pyridinium represented by the following Formula (1), 4-substituted phenylsulfonate represented by the following Formula (2a), and 2,4,6-substituted phenylsulfonate represented by the following Formula (2b).

(Continued)

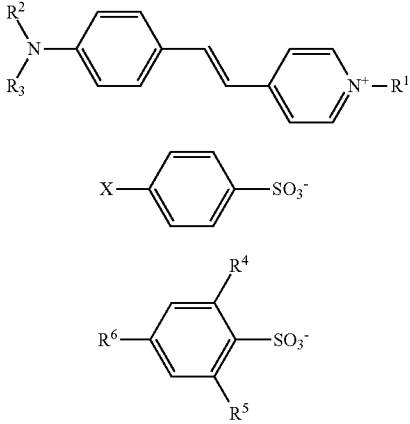

10 Claims, 6 Drawing Sheets (51) Int. Cl.
    *C07D 213/38*    (2006.01)
    *C07D 401/04*    (2006.01)
    *G01N 21/3581*   (2014.01)
    *C07C 309/30*    (2006.01)

(52) U.S. Cl.
    CPC ....... *G01N 21/3581* (2013.01); *G02F 1/3551* (2013.01); *G02F 1/3613* (2013.01)

(58) Field of Classification Search
    USPC ...................................... 250/339.02, 339.07
    See application file for complete search history.

(56) References Cited

FOREIGN PATENT DOCUMENTS

| JP | 2009-256165 | * | 11/2009 | ............. C30B 29/54 |
|---|---|---|---|---|
| WO | WO 2008/034272 | * | 3/2008 | |
| WO | WO-2008/034272 A1 | | 3/2008 | |

OTHER PUBLICATIONS

S. Brahadeeswaran, et al., "Growth of Ultrathin and Highly Efficient Organic Nonlinear Optical Crystal 4'-Dimethylamino-N-methyl-4-Stilbazolium p-Chlorobenzenesulfonate for Enhanced Terahertz Efficiency at Higher Frequencies", Crystal Growth and Design, Jan. 10, 2013 vol. 13, No. 2, p. 415-p. 421.

M. Hiratsuka, et al., "Broadband THz generation from DASC crystal", The 53rd Spring Meeting of The Japan Society of Applied Physics and Related Societies, Lecture Proceedings, 2006, No. 3, p. 1178.

T. Matsukawa, et al., "Bulk Crystal Growth of Stilbazolium Derivatives for Terahertz Waves Generation", Japanese Journal of Applied Physics, Jul. 20, 2010, vol. 49, No. 7R, p. 075502-1-p. 075502-6.

B. Monoszlai, et al., "High-energy terahertz pulses from organic crystals: DAST and DSTMS pumped at Ti:sapphire wavelength", Optics Letters, Dec. 1, 2013 vol. 38, No. 23, p. 5106-p. 5109.

T. Taniuchi, et al., "Tunable THz-wave generation from a new organic DAST/DASC mixed crystal", The 53rd Spring Meeting of The Japan Society of Applied Physics and Related Societies, Lecture Proceedings, 2006, No. 3, p. 1177.

English-language translation of International Preliminary Report on Patentability (IPRP) dated Mar. 16, 2017 that issued in WO Patent Application No. PCT/JP2015/074410.

"Research for solution growth of functional organic crystals and application of it for photo-electronic devices," Doctoral Thesis Statement, Osaka University, Japan, 2010, http://hdl.handle.net/11094/1083.

Akio Okazaki, et al., "Access Control System with Automatic Logging for User's Facial Information", The Journal of The Institute of Image Information and Television Engineers, vol. 57, No. 9, Sep. 1, 2003, p. 1168-p. 1176.

J. Ogawa, et al., "Preparation, properties and structures of 1-methyl-4-{2-[4-(dimethylamino)phenyl]ethenyl}pyridinium crystals with various conter anions", Journal of Crystal Growth, 2008, vol. 310, pp. 836-842.

T. Matsukawa, et al., "Synthesis and terahertz-wave generation of mixed crystals composed of 1-methyl-4-{2-[4-(dimethylamino)phenyl]ethenyl}pyridinium p-toluenesulfonate and p-chlorobenzenesulfonate", Journal of Crystal Growth, 2007, vol. 299, pp. 344-348.

\* cited by examiner

NON-LINEAR OPTICAL CRYSTAL AND METHOD FOR MANUFACTURING SAME, AND TERAHERTZ-WAVE GENERATOR AND TERAHERTZ-WAVE MEASURING APPARATUS

TECHNICAL FIELD

The present invention relates to a non-linear optical crystal, a method for manufacturing the same, a terahertz-wave generating element, a terahertz-wave generator, and a terahertz-wave measuring apparatus.

BACKGROUND ART

Applying organic crystals having non-linear optical effects as terahertz-wave generating elements or terahertz-wave detecting elements has been studied.

In general, the intensity of terahertz waves generated from non-linear optical crystals varies depending on frequencies, but the frequency range in which the intensity of the terahertz waves is lowered varies depending on the type of compounds constituting non-linear optical crystals. In this regard, there is proposed a technique in which plural kinds of substituted phenylsulfonate providing crystals having different ranges in which the output is lowered are combined with respect to a non-linear optical crystal containing a salt of pyridinium and substituted phenylsulfonate so that terahertz waves with a sufficient output intensity are generated in a wide range (for example, Patent Literature 1).

CITATION LIST

Patent Literature

Patent Literature 1: Japanese Unexamined Patent Publication No. 2007-328145

SUMMARY OF INVENTION

Technical Problem

However, even in the case of combining plural kinds of salts as described in Patent Literature 1, the output intensity of the terahertz wave may be locally lowered in a particular frequency range in some cases. Specifically, the salt of pyridinium and substituted phenylsulfonate has a large decrease in output intensity of the terahertz wave near 1 THz, and thus there is room for improvement particularly in this point.

In this regard, a main object of the present invention is to sufficiently suppress a local decrease in output of a non-linear optical crystal formed from an organic material in a frequency range near 1 THz and to maintain a stable output intensity in a wide range.

Solution to Problem

An aspect of the present invention relates to a non-linear optical crystal containing pyridinium represented by the following Formula (1), 4-substituted phenylsulfonate represented by the following Formula (2a), and 2,4,6-substituted phenylsulfonate represented by the following Formula (2b). In Formula (1), $R^1$, $R^2$, and $R^3$ each independently represent a methyl group or an ethyl group. In Formula (2a), X represents a halogen atom, and in Formula (2b), $R^4$, $R^5$, and $R^6$ each independently represent a methyl group or an ethyl group.

According to the non-linear optical crystal, by using pyridinium of Formula (1) as a cation and combining this pyridinium with two kinds of substituted phenylsulfonate of Formula (2a) and Formula (2b) each having a different substituent of a phenyl group as anions, it is possible to sufficiently suppress a local decrease in output in a frequency range near 1 THz and to maintain a stable output intensity in a wide range. Regarding each of the crystal formed from pyridinium of Formula (1) and 4-substituted phenylsulfonate of Formula (2a) and the crystal formed from pyridinium of Formula (1) and 4-methyl phenylsulfonate, a local decrease in output intensity near 1 THz is recognized. However, according to the finding of the present inventors, in the non-linear optical crystal obtained by combining pyridinium with two kinds of substituted phenylsulfonate respectively represented by Formula (2a) and Formula (2b) as anions, a decrease in output intensity near 1 THz is significantly suppressed.

$R^1$, $R^2$, and $R^3$ in Formula (1) each may be a methyl group, X in Formula (2a) may be a chlorine atom, and $R^4$, $R^5$, and $R^6$ in Formula (2b) each may be a methyl group. Accordingly, the effect of suppressing a local decrease in output is particularly significantly exhibited.

In another aspect, the present invention relates to a method for manufacturing the non-linear optical crystal. The method includes a step of precipitating the non-linear optical crystal from a solution containing the pyridinium, the 4-substituted phenylsulfonate, the 2,4,6-substituted phenylsulfonate, and a solvent in which the pyridinium, the 4-substituted phenylsulfonate, and the 2,4,6-substituted phenylsulfonate are dissolved.

In still another aspect, the present invention provides a terahertz-wave generator and a terahertz-wave measuring apparatus which include a terahertz-wave generating element including the non-linear optical crystal. The terahertz-wave generator according to the present invention can generate a terahertz wave with high stability in which a local decrease in output intensity is suppressed. According to the terahertz-wave measuring apparatus related to the present invention, stable spectroscopic analysis or the like can be performed in a wide range by using a terahertz wave.

The present invention can also provide a terahertz-wave detecting apparatus which includes a terahertz-wave detecting element including the non-linear optical crystal. According to the terahertz-wave detecting element, stable spectroscopic analysis or the like can also be performed in a wide range by using a terahertz wave.

Advantageous Effects of Invention

According to the present invention, it is possible to sufficiently suppress a local decrease in output of a non-linear optical crystal formed from an organic material in a frequency range near 1 THz and to maintain a stable output intensity in a wide range.

DESCRIPTION OF EMBODIMENTS

Hereinafter, embodiments of the present invention will be described in detail. However, the present invention is not limited to the following embodiments. In the descriptions of the drawings, components identical or equivalent to each other are attached with the same reference symbols, and overlapping description may be omitted.

A crystal according to an embodiment is comprised of: pyridinium represented by the following Formula (1); and 4-substituted phenylsulfonate represented by the following Formula (2a), and 2,4,6-substituted phenylsulfonate represented by the following Formula (2b). The crystal may be a mixed crystal comprised of two kinds of salts including: a salt of pyridinium represented by Formula (1) and 4-substituted phenylsulfonate represented by Formula (2a); and a salt of pyridinium represented by Formula (1) and 2,4,6-substituted phenylsulfonate represented by Formula (2b). This crystal is a non-linear optical crystal showing a non-linear response to incident light and can generate particularly light of a terahertz wave band.

(1)

(2a)

(2b)

In Formula (1), $R^1$, $R^2$, and $R^3$ each independently represent a methyl group or an ethyl group. In Formula (2a), X represents a halogen atom (a fluorine atom, a chlorine atom, a bromine atom, or an iodine atom), in Formula (2b), $R^4$, $R^5$, and $R^6$ each independently represent a methyl group or an ethyl group.

A combination of the substituents $R^1$ to $R^3$ and X in each formula can be appropriately selected so that a non-linear optical crystal containing the compounds are formed. For example, $R^1$, $R^2$, and $R^3$ in Formula (1) each may be a methyl group, X in Formula (2a) may be a chlorine atom, and $R^4$, $R^5$, and $R^6$ in Formula (2b) each may be a methyl group.

A ratio of 4-substituted phenylsulfonate of Formula (2a) and 2,4,6-substituted phenylsulfonate of Formula (2b) in the crystal can be appropriately adjusted in a range that enables a desired non-linear optical response to be obtained. For example, the molar ratio of 4-substituted phenylsulfonate of Formula (2a) and 2,4,6-substituted phenylsulfonate of Formula (2b) may be 1:99 to 99:1 when the total of 4-substituted phenylsulfonate and 2,4,6-substituted phenylsulfonate is assumed to be 100.

The crystal according to the embodiment can be obtained by a method including a step of preparing a solution containing pyridinium of Formula (1), 4-substituted phenylsulfonate of Formula (2a), 2,4,6-substituted phenylsulfonate of Formula (2b), and a solvent in which pyridinium, 4-substituted phenylsulfonate, and 2,4,6-substituted phenylsulfonate are dissolved, and a step of precipitating a crystal from this solution.

The solution used for precipitating a crystal can be prepared by respectively preparing a salt of pyridinium of Formula (1) and 4-substituted phenylsulfonate of Formula (2a) and a salt of pyridinium of Formula (1) and 2,4,6-substituted phenylsulfonate of Formula (2b) and then dissolving these salts in a solvent. Each salt can be synthesized by a person skilled in the art according to an ordinary synthesis method, and some salts are commercially available. For example, each salt can be synthesized by a method using, as a starting material, a salt containing pyridinium of Formula (1) as a cation and replacing an anion of the salt with sulfonate of Formula (2a) or Formula (2b).

When the solution is prepared, the solution may be heated at a predetermined temperature (for example, 45° C.) as necessary. In order to efficiently precipitate the crystal, each salt may be dissolved in a solvent to have a saturation concentration.

The solvent used for preparing the solution is not particularly limited as long as it enables crystallization (recrystallization) of the salt, and examples thereof may include methanol, ethanol, acetonitrile, ethyl acetate, chloroform, acetone, and a combination thereof. By using these solvents, the crystal according to this embodiment can be efficiently produced.

In order to precipitate the crystal from the solution, the temperature of the solution can be continuously or intermittently decreased. For example, the temperature of the solution may be decreased at a cooling rate of 0.1 to 1° C./day.

The crystal precipitated and grown in the solution is extracted from the solution. The extracted crystal is processed into a desired shape and size as necessary. The maximum thickness of the crystal may be, for example, 0.1 to 2 mm.

The crystal (non-linear optical crystal) according to this embodiment described above can be used as a terahertz-wave generating element or a terahertz-wave detecting element as illustrated below.

Figure 1:
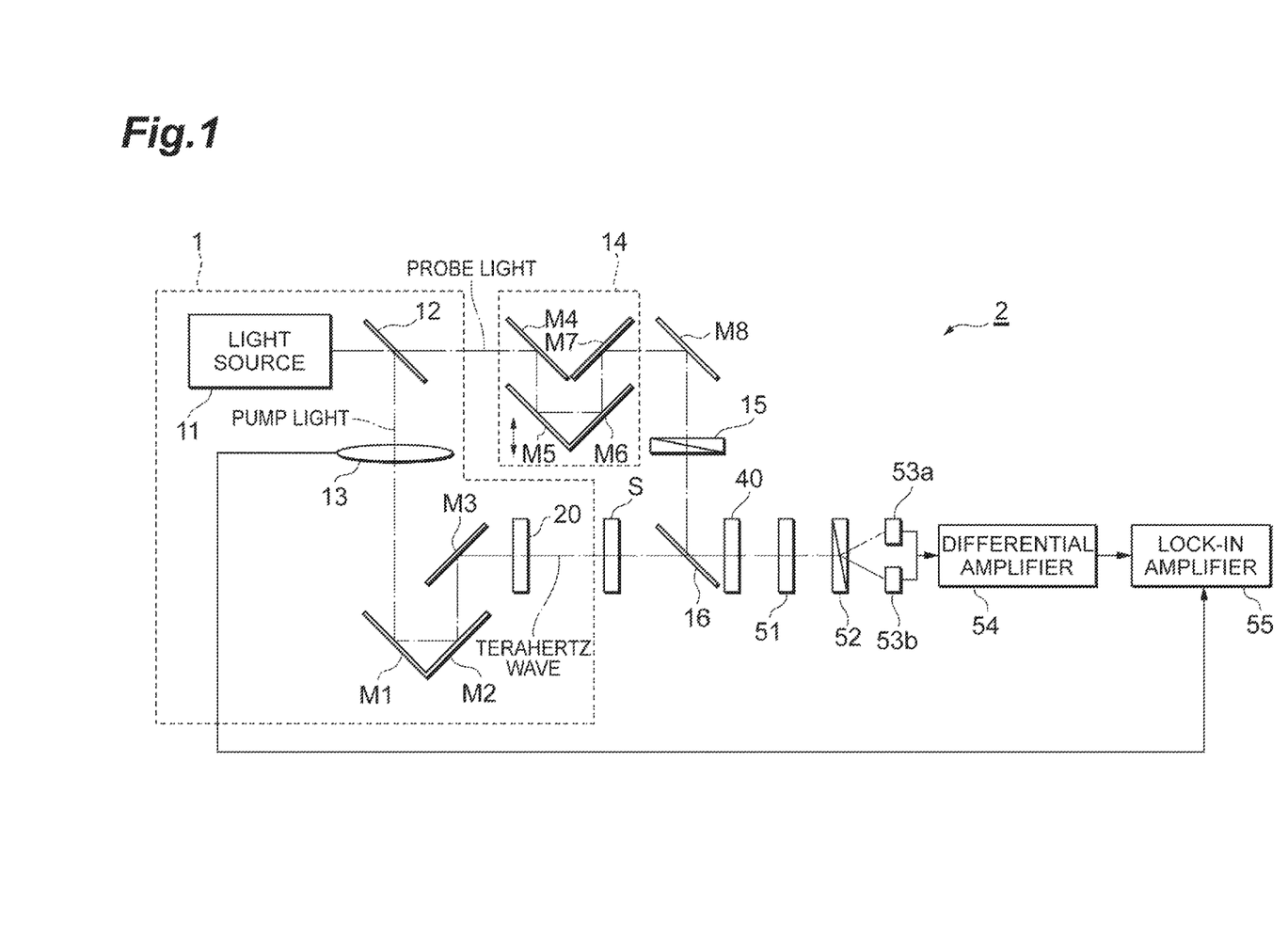
FIG. 1 is a diagram illustrating an embodiment of a terahertz-wave measuring apparatus.

FIG. 1 is a diagram illustrating an embodiment of a terahertz-wave measuring apparatus. A terahertz-wave measuring apparatus 2 illustrated in FIG. 1 is configured to acquire information on a measuring object S by a transmission measurement method by use of a terahertz wave. The terahertz-wave measuring apparatus 2 includes a light source 11, a branching part 12, a chopper 13, an optical path length difference adjusting part 14, a polarizer 15, a coupling part 16, a terahertz-wave generating element 20, a terahertz-wave detecting element 40, a quarter-wavelength plate 51, a polarization split element 52, a photodetector 53a, a photodetector 53b, a differential amplifier 54, and a lock-in amplifier 55. As the terahertz-wave generating element 20 and/or the terahertz-wave detecting element 40, the crystal according to this embodiment can be used.

The light source 11 is to output pulsed light at a constant repetition period, and for example, may be a femtosecond pulsed laser light source that outputs pulsed laser light whose pulse width is approximately femtoseconds. The wavelength of light output from the light source 11 may be, for example, 700 to 1600 nm.

The branching part 12 branches the pulsed light output from the light source 11 into two components, outputs one component of the pulsed light branched into two components to a mirror M1 as pump light, and outputs the other component to a mirror M4 as probe light. The branching part 12 may be, for example, a beam splitter.

The chopper 13 is provided on an optical path of the pump light between the branching part 12 and the mirror M1 to repeat alternately passage and blocking of the pump light at a constant period. The pump light output from the branching part 12 to pass through the chopper 13 is sequentially reflected by mirrors M1 to M3 to be input to the terahertz-wave generating element 20. An optical system for the pump light from the branching part 12 up to the terahertz-wave generating element 20 is hereinafter called a "pump optical system."

The terahertz-wave generator 1 is configured by the light source 11, the branching part 12, the chopper 13, the mirror M1, the mirror M2, the mirror M3, and the terahertz-wave generating element 20 in the pump optical system. The terahertz-wave generator may be configured to include the light source and the terahertz-wave generating element and to input the pulsed light output from the light source to the terahertz-wave generating element, and other configurations of the terahertz-wave generator is arbitrary.

The terahertz-wave generating element 20 generates and outputs a pulsed terahertz wave by allowing the pump light to be input thereto. The pulsed terahertz wave is generated at a constant repetition period and the pulse width thereof is approximately several picoseconds. The terahertz wave output from the terahertz-wave generating element 20 is transmitted through the measuring object S to acquire information on the measuring object S (for example, an absorption coefficient or a refractive index), and thereafter, the terahertz wave is input to the coupling part 16. An optical system of the terahertz wave from the terahertz-wave generating element 20 up to the coupling part 16 is hereinafter called a "terahertz wave optical system." In the present specification, as the terahertz wave, an electromagnetic wave having a frequency in a range of approximately 0.01 THz to 100 THz is mainly assumed.

On the other hand, the probe light output from the branching part 12 is sequentially reflected by mirrors M4 to M8 and passes through the polarizer 15 to be input to the coupling part 16. An optical system of the probe light from the branching part 12 up to the coupling part 16 is hereinafter called a "probe optical system." The four mirrors M4 to M7 constitute the optical path length difference adjusting part 14.

The terahertz wave output from the terahertz-wave generating element 20 to transmitted through the measuring object S and the probe light output from the branching part 12 to reach the coupling part 16 are input to the coupling part 16, and these terahertz wave and probe light are coupled so as to be coaxial with each other and output the coupled terahertz wave and probe light to the terahertz-wave detecting element 40. The coupling part 16 may be a pellicle having a support frame forming an opening and a film type mirror attached to the support frame.

A correlation between the terahertz wave and the probe light is detected by the terahertz-wave detecting element 40. The terahertz-wave detecting element 40 may include the non-linear optical crystal according to the aforementioned embodiment or may include another electro-optic crystal.

The polarization split element 52 inputs the probe light output from the terahertz-wave detecting element 40 to go through the quarter-wavelength plate 51, splits the input probe light into two polarization components perpendicular to each other, and then outputs the polarization components. The polarization split element 52 may be, for example, a Wollaston prism. The photodetectors 53a and 53b include, for example, photodiodes, detect powers of the two polarization components of the probe light split to be polarized by the polarization split element 52, and then output electric signals having values corresponding to the detected powers to the differential amplifier 54.

The differential amplifier 54 inputs the electric signals respectively output from the photodetectors 53a and 53b and outputs an electric signal having a value corresponding to a difference between the values of both electric signals to the lock-in amplifier 55. The lock-in amplifier 55 synchronously detects the electric signal output from the differential amplifier 54 at a repetition frequency of passage and blocking of the pump light by the chopper 13. The signal output from the lock-in amplifier 55 has a value dependent on an electric field intensity of the terahertz wave. In this way, it is possible to acquire information on the measuring object S by detecting a correlation between the terahertz wave which is transmitted through the measuring object S and the probe light to detect an electric field amplitude of the terahertz wave.

Figure 2:
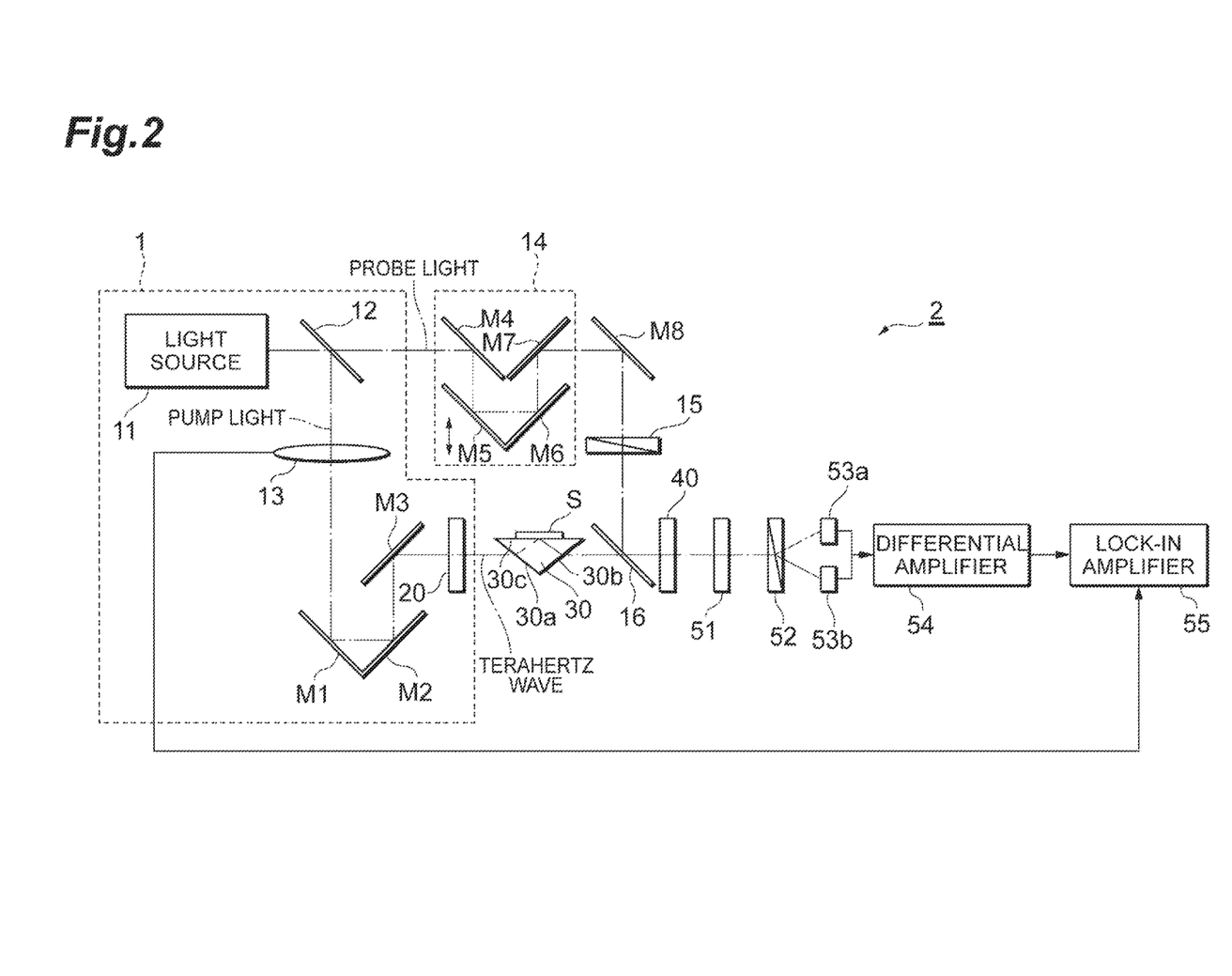
FIG. 2 is a diagram illustrating an embodiment of a terahertz-wave measuring apparatus.

Like the terahertz-wave measuring apparatus 2 illustrated in FIG. 2, a prism 30 having an entrance surface 30a, an exit surface 30b, and a reflection surface 30c may be provided on the terahertz wave optical system between the terahertz-wave generating element 20 and the coupling part 16, and the measuring object S may be provided on the reflection surface 30c. The terahertz wave output from the terahertz-wave generating element 20 is input to the entrance surface 30a, the input terahertz wave is propagated inside the prism 30 and totally reflected by the reflection surface 30c, and the totally-reflected terahertz wave is output from the exit surface 30b to the coupling part 16. When the terahertz wave is totally reflected by the reflection surface 30c, information on a portion of the measuring object S near the reflection surface 30c is acquired. That is, the terahertz-wave measuring apparatus 2 of FIG. 2 is a total reflection terahertz-wave measuring apparatus.

Figure 3:
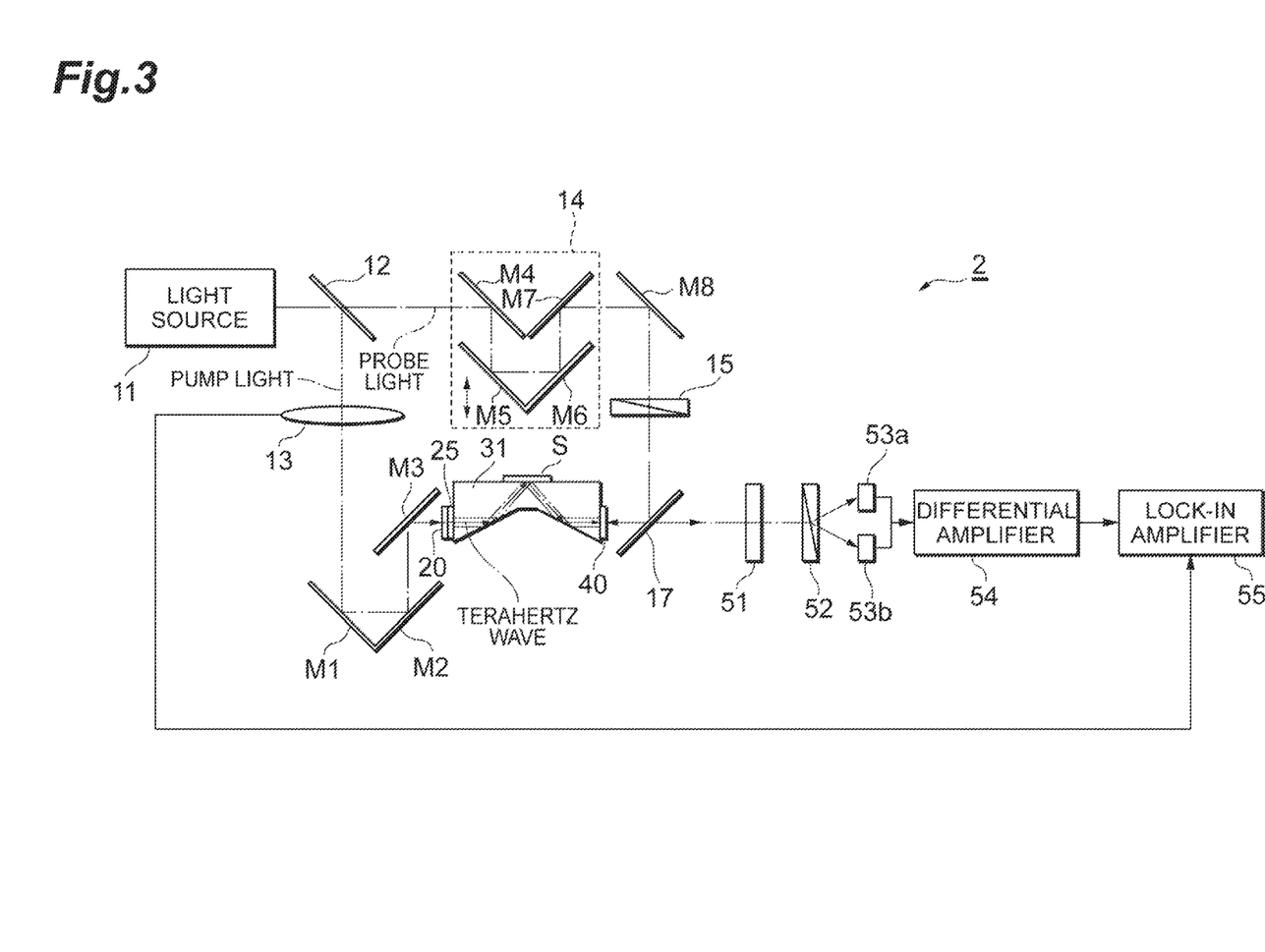
FIG. 3 is a diagram illustrating an embodiment of a terahertz-wave measuring apparatus.

The terahertz-wave measuring apparatus 2 illustrated in FIG. 3 is also a total reflection terahertz-wave measuring apparatus like the case of FIG. 2 and is provided with, an internal total reflection prism 31 instead of the prism 30. The terahertz-wave generating element 20, a filter 25, and the terahertz-wave detecting element 40 are integrally provided with the internal total reflection prism 31. In addition, a beam splitter 17 is provided instead of the coupling part 16. The beam splitter 17 may be a pellicle.

Figure 4:
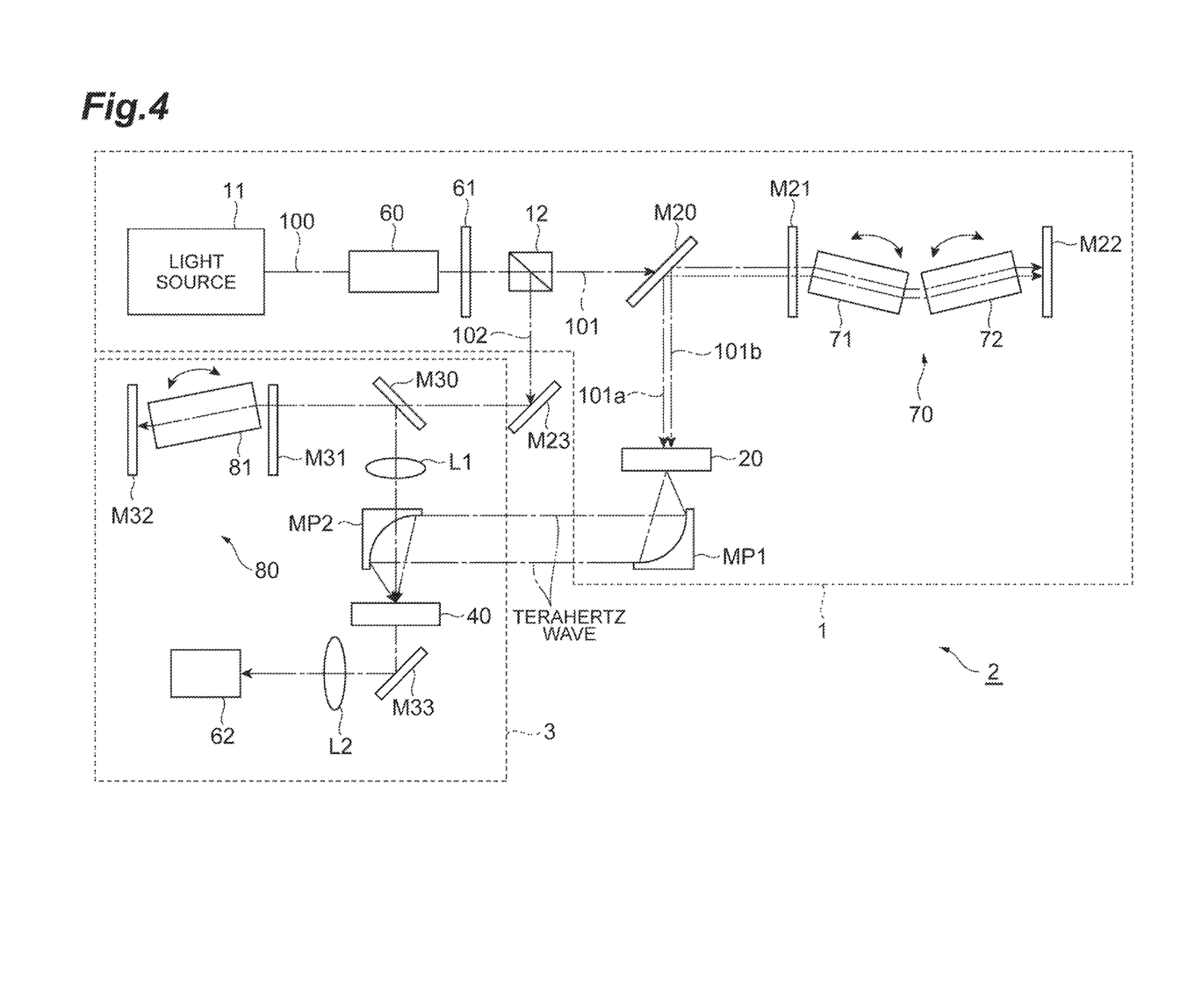
FIG. 4 is a diagram illustrating an embodiment of a terahertz-wave measuring apparatus.

FIG. 4 is also a diagram illustrating an embodiment of the terahertz-wave measuring apparatus. The terahertz-wave measuring apparatus 2 illustrated in FIG. 4 is provided with the terahertz-wave generator 1, which is configured by the light source 11, an optical isolator 60, a half-wavelength plate 61, the branching part 12, a mirror M20, a dual-wavelength parametric oscillator 70, the terahertz-wave generating element 20, and a concave mirror MP1, and a terahertz-wave detecting apparatus 3. As the terahertz-wave generating element 20, the crystal according to the aforementioned embodiment can be used.

The dual-wavelength parametric oscillator 70 includes mirrors M21 and M22 facing each other on the optical path and two bulk KTP crystals 71 and 72 sequentially provided on the optical path between the mirrors M21 and M22.

The terahertz-wave detecting apparatus 3 includes a mirror M30, an optical parametric oscillator 80, a lens L1, a concave mirror MP2, a terahertz-wave detecting element 40, a mirror M33, a lens L2, and a photodetector 62. The optical parametric oscillator 80 includes mirrors M31 and M32 facing each other on the optical path and a bulk KTP crystal 81 provided on the optical path between the mirrors M31 and M32. The terahertz-wave detecting element 40 may include the crystal according to the aforementioned embodiment or may include another electro-optic crystal.

Pulsed light 100 output from the light source 11 is transmitted through the optical isolator 60 and the half-wavelength plate 61 and then is branched into two components at the branching part 12. One component of the branched light is output as pump light 101 to the mirror M20, and the other component is output as probe light 102 to the mirror M23. The pump light 101 is transmitted through the mirror M20 to be input to the dual-wavelength parametric oscillator 70 and dual-wavelength pump light beams 101a and 101b are output from the dual-wavelength parametric oscillator 70. The pump light beams 101a and 101b are reflected by the mirror M20 to be input to the terahertz-wave generating element 20. The terahertz-wave generating element 20 outputs a terahertz wave and the terahertz wave is reflected by the concave mirror MP1 in a direction toward the concave mirror MP2 of the terahertz-wave detecting apparatus 3.

The probe light 102 output from the branching part 12 is reflected by the mirror M23 to be transmitted through the mirror M30 and then input to the optical parametric oscillator 80 of the terahertz-wave detecting apparatus 3. The probe light 102 output from the parametric oscillator is reflected by the mirror M30 to be transmitted through the lens L1 and the concave mirror MP2 and then input to the terahertz-wave detecting element 40 together with the terahertz wave.

Light output from the terahertz-wave detecting element 40 is reflected by the mirror M33 to be transmitted through the lens L2 and then input to the photodetector 62. The photodetector 62 may be, for example, an InGaAs photodetector.

Figure 5:
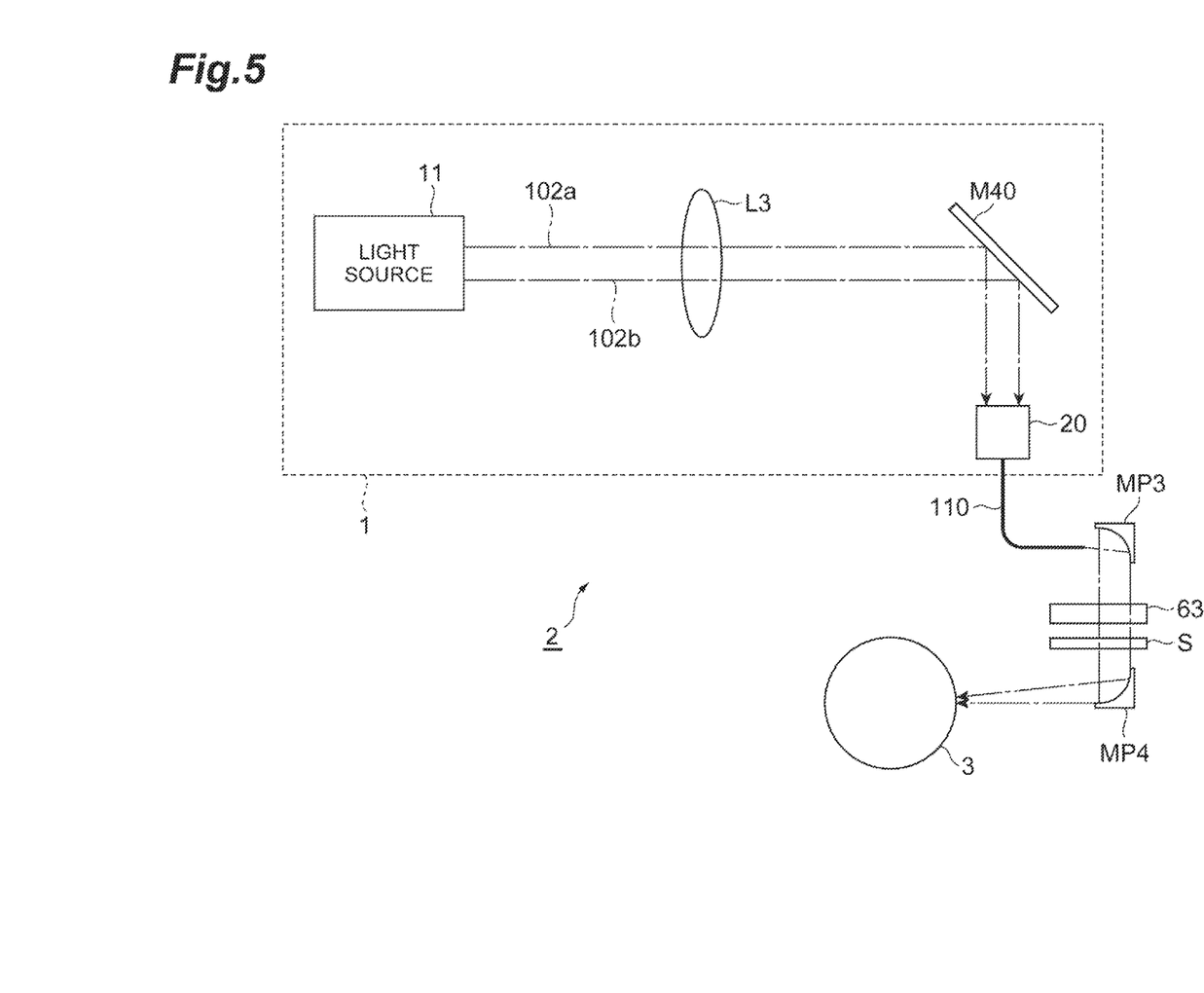
FIG. 5 is a diagram illustrating an embodiment of a terahertz-wave measuring apparatus.

FIG. 5 is also a diagram illustrating an embodiment of the terahertz-wave measuring apparatus. The terahertz-wave measuring apparatus 2 illustrated in FIG. 5 is provided with the terahertz-wave generator 1, which is configured by the light source 11, a lens L3, a mirror M40, and the terahertz-wave generating element 20, a hollow transmission pipe 110, a concave mirror MP3, a low-pass filter 63, a concave mirror MP4, and the terahertz-wave detecting apparatus 3. As the terahertz-wave generating element 20, the crystal according to the aforementioned embodiment can be used.

The light source 11 outputs dual-wavelength probe light (pulsed light) beams 102a and 102b. The probe light beams 102a and 102b are reflected by the mirror M40 to be input to the terahertz-wave generating element 20. A terahertz wave output from the terahertz-wave generating element 20 is transmitted by the hollow transmission pipe 110 to be output to the concave mirror MP3. The terahertz wave reflected by the concave mirror MP3 is transmitted through the low-pass filter 63 to be input to the measuring object S. The light transmitted through the measuring object S to be reflected by the concave mirror MP4 is input to the terahertz-wave detecting apparatus 3.

EXAMPLES

Hereinafter, the present invention will be described in more detail by means of Examples. However, the present invention is not limited to these Examples.

1. Raw Material

DASC, DSTMS, and DAST powders described below were synthesized according to an ordinary method.

DASC:
a salt of pyridinium represented by Formula (1) in which $R^1$, $R^2$, and $R^3$ each are a methyl group and 4-chlorophenylsulfonate represented by Formula (2a) in which X is a chlorine atom DSTMS:
a salt of pyridinium represented by Formula (1) in which $R^1$, $R^2$, and $R^3$ each are a methyl group and 2,4,6-trimethyl phenylsulfonate represented by Formula (2b) in which $R^4$, $R^5$, and $R^6$ each are a methyl group DAST:
a salt of pyridinium represented by Formula (1) in which $R^1$, $R^2$, and $R^3$ each are a methyl group and 4-methyl phenylsulfonate 2. Preparation of Crystal DASC/DSTMS Crystal (Mixed Crystal)

Into 150 mL of methanol, 1.7 g of DASC and 1.7 g of DSTMS were put. DASC and DSTMS were dissolved in methanol by performing heating for 24 hours in a thermostat bath at 45° C. Then, undissolved solid matters were removed through filtration to thereby obtain a saturated solution with a temperature of 45° C. The saturated solution with a temperature of 45° C. was gradually cooled at a rate of 0.5° C./day to precipitate a mixed crystal containing DASC and DSTM.

DAST Crystal and DSTMS Crystal

A DAST crystal and a DSTMS crystal were prepared in the same procedures as in the mixed crystal.

3. Evaluation

The DASC/DSTMS crystal, the DAST crystal, and the DSTMS crystal were subjected to irradiation with pulsed laser light (wavelength: 1550 nm, repetition frequency: 80 MHz), respectively. Terahertz waves generated from the crystals through irradiation with pulsed laser light were measured by using a PC antenna serving as a THz wave detecting element.

Figure 6:
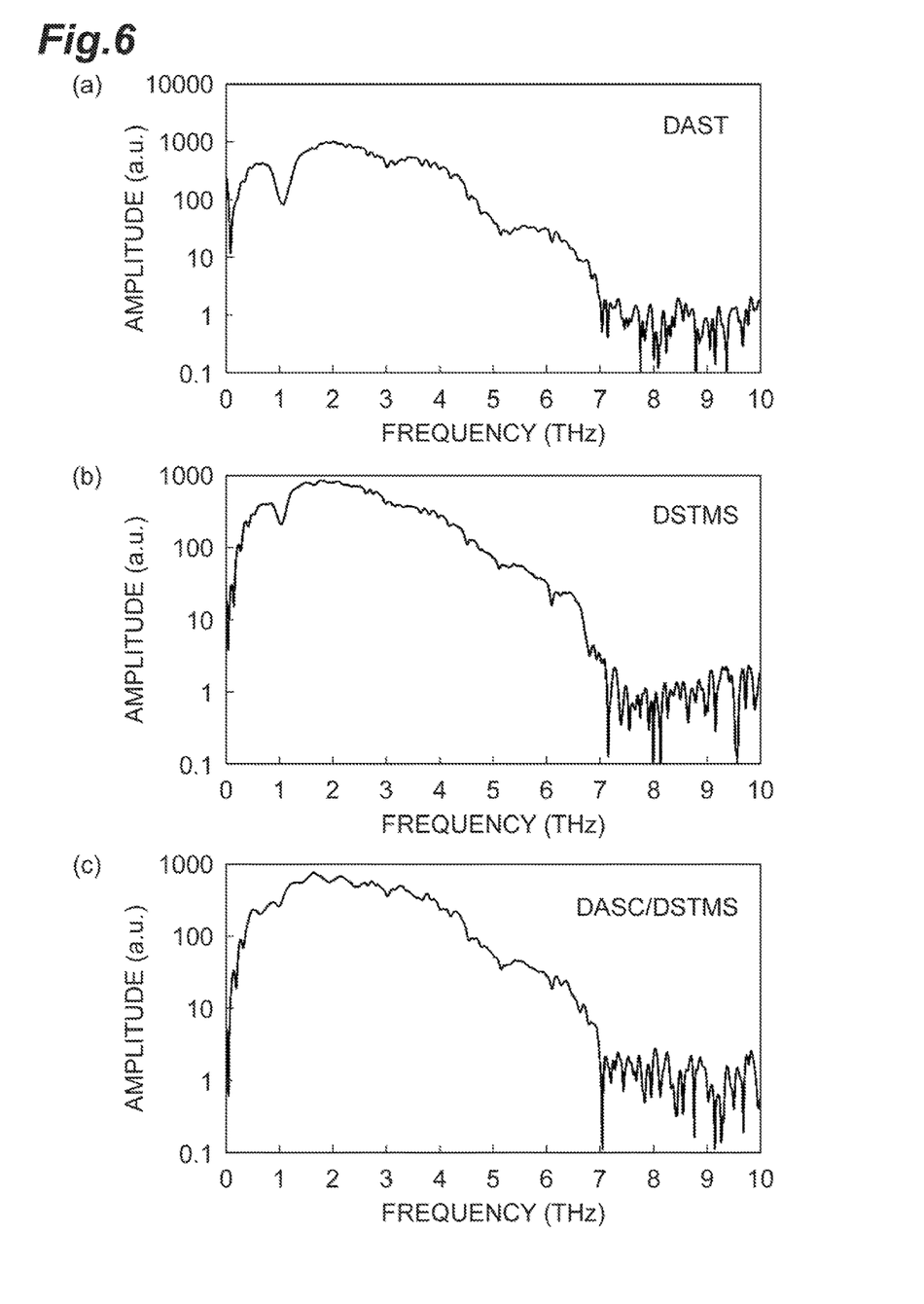
FIG. 6 is a graph showing a relation between the intensity of emitted light of a non-linear optical crystal and a frequency.

FIG. 6 is a graph showing a relation between the intensity (amplitude) of emitted light of each crystal and a frequency thereof. In FIG. 6, (a), (b), and (c) show the evaluation results of the DAST crystal, the DSTMS crystal, and the DASC/DSTMS crystal, respectively. In the case of the DAST crystal and the DSTMS crystal, a local decrease in output intensity near 1 THz was recognized; on the other hand, in the case of the DASC/DSTMS crystal that is a mixed crystal of DASC and DSTMS, a decrease in output intensity near 1 THz was not substantially recognized.

REFERENCE SIGNS LIST

1 . . . terahertz-wave generator, 2 . . . terahertz-wave measuring apparatus, 3 . . . terahertz-wave detecting apparatus, 11 . . . light source, 12 . . . branching part, 13 . . . chopper, 14 . . . optical path length difference adjusting part, 15 . . . polarizer, 16 . . . coupling part, 17 . . . beam splitter, 20 . . . terahertz-wave generating element, 25 . . . filter, 30 . . . prism, 30a . . . entrance surface, 30b . . . exit surface, 30c . . . reflection surface, 31 . . . internal total reflection prism, 40 . . . terahertz-wave detecting element, 51 . . . quarter-wavelength plate, 52 . . . polarization split element, 53a, 53b . . . photodetector, 54 . . . differential amplifier, 55 . . . lock-in amplifier, 60 . . . optical isolator, 61 . . . half-wavelength plate, 62 photodetector, 63 . . . low-pass filter, 70 . . . dual-wavelength parametric oscillator, 71, 72 . . . bulk KTP crystal, 80 . . . optical parametric oscillator, 81 . . . bulk KTP crystal, 100 . . . pulsed light, 101, 101a, 101b . . . pump light, 102, 102a, 102b . . . probe light, 110 . . . hollow transmission pipe, L1, L2, L3 . . . lens, MP1, MP2, MP3, MP4 . . . concave mirror, S . . . measuring object.

The invention claimed is:

1. A non-linear optical crystal comprising:
pyridinium represented by the following Formula (1); and 4-substituted phenylsulfonate represented by the following Formula (2a) and 2,4,6-substituted phenylsulfonate represented by the following Formula (2b), (1)

In Formula (1), $R^1$, $R^2$, and $R^3$ each independently represent a methyl group or an ethyl group, (2a)

(2b)

In Formula (2a), X represents a halogen atom, and in Formula (2b), $R^4$, $R^5$, and $R^6$ each independently represent a methyl group or an ethyl group, wherein the non-linear optical crystal generates terahertz waves with a suppressed local decrease in output intensity in emitted light near 1 THz compared to a crystal made of a salt of the pyridinium represented by Formula (1) and the 2,4,6-substituted phenylsulfonate represented by Formula (2b), the non-linear optical crystal comprises a mixed crystal of two salts, a first of the two salts being the pyridinium represented by Formula (1) and 4-substituted phenylsulfonate represented by Formula (2a), and a second of the two salts being pyridinium represented by Formula (1) and 2,4,6-substituted phenylsulfonate represented by Formula (2b).

2. The non-linear optical crystal according to claim 1, wherein $R^1$, $R^2$, and $R^3$ in Formula (1) each are a methyl group, X in Formula (2a) is a chlorine atom, and $R^4$, $R^5$, and $R^6$ in Formula (2b) each are a methyl group.

3. A method for manufacturing the non-linear optical crystal according to claim 2, the method comprising:
precipitating the non-linear optical crystal from a solution containing the pyridinium, the 4-substituted phenylsulfonate, the 2,4,6-substituted phenylsulfonate, and a solvent in which the pyridinium, the 4-substituted phenylsulfonate, and the 2,4,6-substituted phenylsulfonate are dissolved.

4. A terahertz-wave generator comprising a terahertz-wave generating element including the non-linear optical crystal according to claim 2.

5. A terahertz-wave measuring apparatus comprising a terahertz-wave generating element including the non-linear optical crystal according to claim 2.

6. A terahertz-wave measuring apparatus comprising a terahertz-wave detecting element including the non-linear optical crystal according to claim 2.

7. A method for manufacturing the non-linear optical crystal according to claim 1, the method comprising:
precipitating the non-linear optical crystal from a solution containing the pyridinium, the 4-substituted phenylsulfonate, the 2,4,6-substituted phenylsulfonate, and a solvent in which the pyridinium, the 4-substituted phenylsulfonate, and the 2,4,6-substituted phenylsulfonate are dissolved.

8. A terahertz-wave generator comprising a terahertz-wave generating element including the non-linear optical crystal according to claim 1.

9. A terahertz-wave measuring apparatus comprising a terahertz-wave generating element including the non-linear optical crystal according to claim 1.

10. A terahertz-wave measuring apparatus comprising a terahertz-wave detecting element including the non-linear optical crystal according to claim 1.

* * * * *